United States Patent [19]
Fujii

[11] Patent Number: 5,810,167
[45] Date of Patent: Sep. 22, 1998

[54] INFECTIOUS WASTE CONTAINER FOR BLOOD COLLECTION NEEDLES

[75] Inventor: Tsuguo Fujii, Ohtsu, Japan

[73] Assignee: Nissho Corporation, Osaka-fu, Japan

[21] Appl. No.: 901,636

[22] Filed: Jul. 28, 1997

[30] Foreign Application Priority Data

Jul. 31, 1996 [JP] Japan .................................. 8-202450

[51] Int. Cl.[6] .................................................. B65D 83/10
[52] U.S. Cl. ........................... 206/365; 206/366; 604/192
[58] Field of Search .................................. 206/365, 366, 206/370; 604/110, 192, 198

[56] References Cited

U.S. PATENT DOCUMENTS

| | | | |
|---|---|---|---|
| 5,092,462 | 3/1992 | Sagstetter et al. .................. | 206/366 |
| 5,312,346 | 5/1994 | Han .................................. | 604/110 |
| 5,347,078 | 9/1994 | Eckels .............................. | 206/365 |
| 5,409,112 | 4/1995 | Sagstetter ......................... | 206/366 |
| 5,409,113 | 4/1995 | Richardson et al. . | |
| 5,474,181 | 12/1995 | Shillington et al. ............... | 206/366 |
| 5,601,532 | 2/1997 | Gaba .................................. | 604/110 |

FOREIGN PATENT DOCUMENTS

0780136A2   6/1997   European Pat. Off. .

Primary Examiner—David T. Fidei
Attorney, Agent, or Firm—Birch, Stewart, Kolasch & Birch, LLP

[57] ABSTRACT

An infectious waste container for blood collection needles comprises a container body (1) for containing blood collection needles, a lid body (2) attached to the container body (1), and needle-removing means (3) attached to the lid body (1) for removing a blood collection needle from a blood collection needle holder, the needle-removing means having a holder insertion section (31) and a holder suspension section (32) and being axisymmetrially provided with first and second notched portions (33, 34) extending from the holder insertion section to the holder suspension section. The first notched portion is stretched to a downwardly slanted portion protruded inwardly from a bottom of the first notched portion, the second notched portion is extended to a position deeper than a level of the slanted portion by a certain distance and terminated within the holder suspension section.

6 Claims, 8 Drawing Sheets

INFECTIOUS WASTE CONTAINER FOR BLOOD COLLECTION NEEDLES

FIELD OF THE INVENTION

The present invention relates to an infectious waste container for blood collection needles, which makes it possible to easily and certainly perform removal and receiving of a blood collection needle from a blood collection needle holder, so-called easily operable blood collection needle holder which makes it possible to remove a used blood collection needle therefrom without touching with operator's fingers.

DESCRIPTION OF THE PRIOR ART

In general, blood collection needles used for sampling the blood from a patient for blood test or blood sedimentation has been fixed to a blood collection needle holder by screw engagement. When removing the used needle from the holder to waste it, this is done by covering the used needle with a protector, disengaging a male screw provided on a hub of the needle from a female screw of the holder, whereby removing the needle together with the protector from the holder. The removed needle covered by the protector is then put into a suitable container.

In this process, however, there is a fear of accidentally injuring a finger or a palm of the hand with the blood collection needle at the time of covering the blood collection needle with the protector. In addition, there is such a danger that the operator is infected with viruses such as AIDS or hepatitis in the worst case.

To solve this problem, there has been developed so-called "an easily operable blood collection needle holder" or a blood collection needle holder so designed as to allow the operator to remove a used blood collection needle without handling it with fingers. Since the easily operable needle holder of the prior art is so designed as to be used in combination with a needle having a specific configuration with a concave or convex portion, it is impossible to use such an easily operable needle holder in combination with the conventional screw mount type needles, thus making it difficult to fix the needle to the holder firmly, different from the screw mount type blood collection needles.

To solve such a problem in the easily operable needle holder of the prior art, the inventors have developed an easily operable needle holder comprising a cylindrical holder body provided with needle-fixing means on a front wall of the holder body. The needle-fixing means includes two sliding members slidable along the front wall of the holder body and is so constructed as to be disengageable with a hub of the needle when one of the sliding members (hereinafter referred to as the "first sliding member") has been slid toward the other sliding member (hereinafter referred to as the "second sliding member"), but engagable with the hub of the needle when the second sliding member has been slid toward the first sliding member. This needle holder makes it possible to fix the needle to the holder firmly by the needle fixing means and can be used in combination with the screw mount type blood collection needles.

On the other hand, the needle can be removed from the holder by sliding the first sliding member toward the second sliding member with the operator's finger, whereby disengaging the needle from the holder, and allowing the needle to fall into a suitable container located just below the needle holder. If the container has a large-sized mouth and if the container containing the used needles is fallen down accidentally, the used needles would be scattered on the floor. This problem may be solved by use of a container with a small-sized mouth, but there is a certain risk of the needle falling from the holder to the outside of the container.

SUMMARY OF THE INVENTION

It is therefore an object of the present invention to provide an infectious waste container for blood collection needles, which makes it possible to perform removal and receiving of a blood collection needle from a needle holder easily and certainly and prevents the needles from scattering even if turned over accidentally.

Another object of the present invention is to provided an infectious waste container for blood collection needles, suitable for use in combination with an easily operable blood collection needle holder which comprises a cylindrical holder body and needle-fixing means provided on a front wall of the holder body.

The above and other objects of the present invention are solved by employing a container having a lid body provided in a top wall thereof with a small-sized opening, and providing needle-removing means in the opening of the lid body for removing a blood collection needle from a blood collection needle holder.

According to the present invention, there is provided an infectious waste container for blood collection needles, hereinafter referred to as a "waste container", comprising a container body with a mouth at a top thereof, a lid body attached to the mouth of said container body and provided in a top wall thereof with an opening, and needle-removing means being arranged in the opening of said lid body for removing a blood collection needle from blood collection needle fixing means of a blood collection needle holder, said needle-removing means comprising a cylindrical member including a holder insertion section and a holder suspension section, said holder insertion section being so formed as to have an inner diameter larger than an outer diameter of said holder, while said holder suspension section being so formed as to have an inner diameter smaller than the outer diameter of said holder, said cylindrical member being axisymmetrially provided with first and second notched portions extending from the holder insertion section to the holder suspension section, said first notched portion being stretched to a downwardly slanted portion protruded inwardly from a bottom of said first notched portion, said first notched portion being terminated at a level where the needle fixing means of said holder does not come into contact with the inner wall of the cylindrical member when said holder is inserted, while the second notched portion being so formed as to be deeper than a level of the slanted portion by a certain distance and terminated within the holder suspension section.

Preferably, the holder insertion section is tapered at a lower part toward the holder suspension section to form a tapered seat for the holder and the first notched portion is terminated at a level slightly below the tapered seat to form a starting point of the slanted portion. In this case, the slanted portion is extended from the bottom of the first notched portion and terminated at a level above the bottom of the second notched portion.

The lid body may be provided with covering means for closing the opening thereof. The covering means may be a freely removable cap provided with at least one rib at a leg portion thereof, or a lid member adapted to open and close the opening of the lid body and has a fixing portion for engagement with the lid body. The fixing portion is connected to the lid member with a connecting portion. The lid member may be provided with a tab or grip adapted to be held in place by slight friction fit with engaging means provided on the top wall of the lid body.

Further, the grip may be provided with one or more projections so that the lid member may be locked in the lid body firmly by press-fitting of the projection into a hole provided in the top wall of the lid body.

The present invention will be explained below, making reference to the accompanying drawings which show a preferred embodiment thereof.

DETAILED DESCRIPTION OF THE PREFERRED EMBODIMENTS

Figure 1:
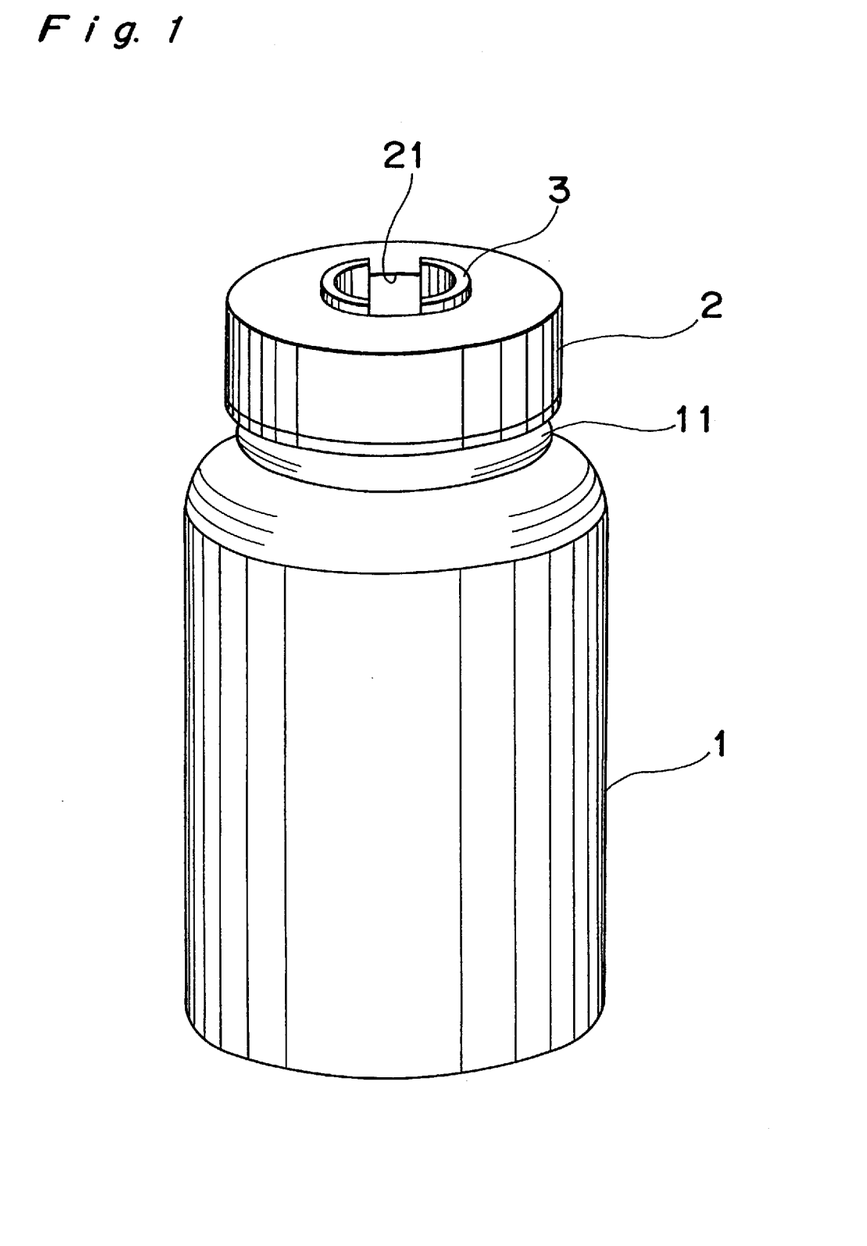
FIG. 1 is an perspective vie of an infectious waste container for blood collection needles according to the present invention.

Referring now to FIG. 1, there is shown a preferred embodiment of an infectious waste container for blood collection needles according to the present invention. The waste container comprises a container body 1 for containing blood collection needles, a lid body 2 mounted on a mouth 11 of the container body 1 and provided at a top wall thereof with an opening 21, and needle-removing means 3 arranged in the lid body 2 to remove a blood collection needle from a blood collection needle holder 6.

As a preferred material for container body 1, lid body 2 and needle-removing means, there may be used synthetic resins such as, for example, polyethylene, polypropylene, polyvinyl chloride, acrylonitrile-butadiene-styrene copolymer, polycarbonate, polyester and the like.

The lid body 2 is attached to the container body 1, preferably by screw mounting or friction fitting. The needle-removing means 3 removes the needle (not illustrated in the drawings) from needle fixing means 7 of the holder 6 and allows the needle to fall into the container body 1. In FIG. 1, the needle-removing means 3 is formed as an independent cylindrical member and attached to the lid body 2, but this needle-removing means may be formed integrally with the lid body 2. In the former case, the attachment of the needle-removing means 3 to the lid body 2 is preferably done by screw mounting, friction-fitting, or by any other means, for example, by tightening the needle removing means 3 with a nut after inserting the needle-removing means 3 into the opening 21 of the lid body 2, or by use of one or more undercuts provided in the needle-removing means 3, or by use of one or more ribs provided on the outer wall of the needle-removing means 3.

Figure 2:
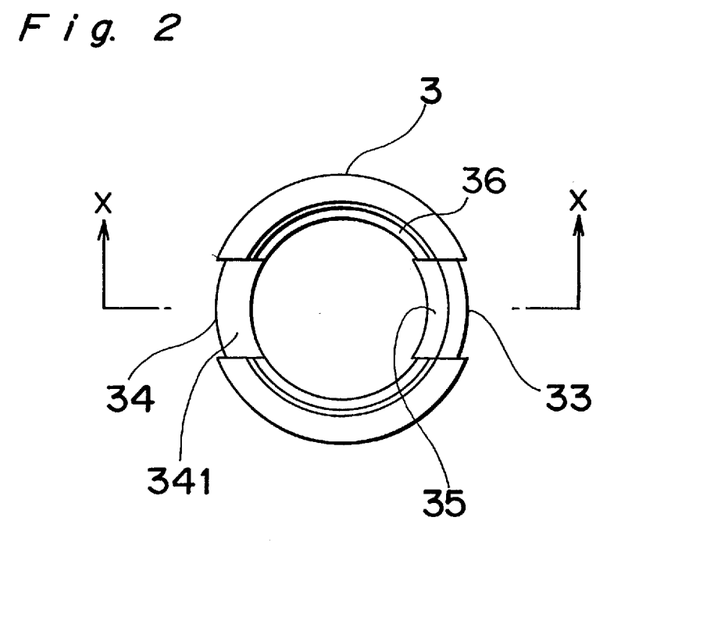
FIG. 2 is a plane view of needle-removing means employed in the waste container of FIG. 1.
Figure 3:
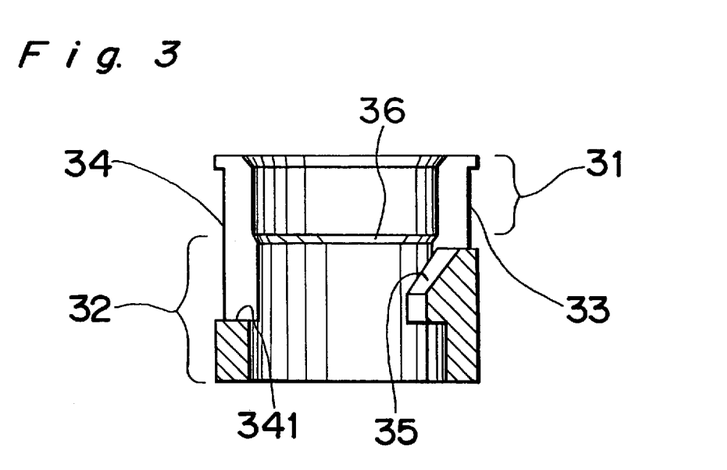
FIG. 3 is a cross section of needle-removing means taken along a line X—X in FIG. 2.

The needle-removing means 3 will be further explained in detail, making reference to FIGS. 1 to 4. As best shown in FIG. 3, the needle-removing means 3 is constituted by a cylindrical member with a flange at a top thereof. The cylindrical member includes a holder insertion section 31 with an inner diameter larger than the outer diameter of the holder 6 and a holder suspension section 32 with an inner diameter smaller than the outer diameter of the holder 6. A lower part of a bore of the holder insertion section 31 may be tapered toward the holder suspension section 32 to form a tapered seat 36 for the holder 6, as illustrated in FIG. 3. Further, an upper part of the bore of the holder insertion section 31 may be enlarged to facilitate insertion of the holder 6.

As illustrated in FIGS. 2 and 3, the cylindrical member 3 is axisymmetrically provided with first and second notched portions 33 and 34, extending from the holder insertion section 31 toward the holder suspension section 32. The first notched portion 33 extends from the top end of the holder insertion section 31 to a part of the holder suspension section 32 and terminates at a level slightly lower than the seat 36, i.e., at a position where the needle fixing means of the holder 6 does not comes into contact with the cylindrical member when the holder 6 is inserted thereinto. The first notched portion 33 is stretched to a downwardly slanted portion 35 protruded inwardly from the bottom of the first notched portion 33. The second notched portion 34 also extends from the top end of the holder insertion section 31 to a part of the holder suspension section 32 and terminates at a level which is lower than lower end of the slanted portion 35 by a certain distance so that the bottom 341 of the second notched portion 34 is located within the holder suspension section 32, as shown in FIG. 3.

Before explaining the needle-removing means 3 in detail, explanation will be made briefly on a blood collection needle holder suitable for use in combination with the waste container of the present invention, making reference to FIGS. 4–7.

Figure 4:
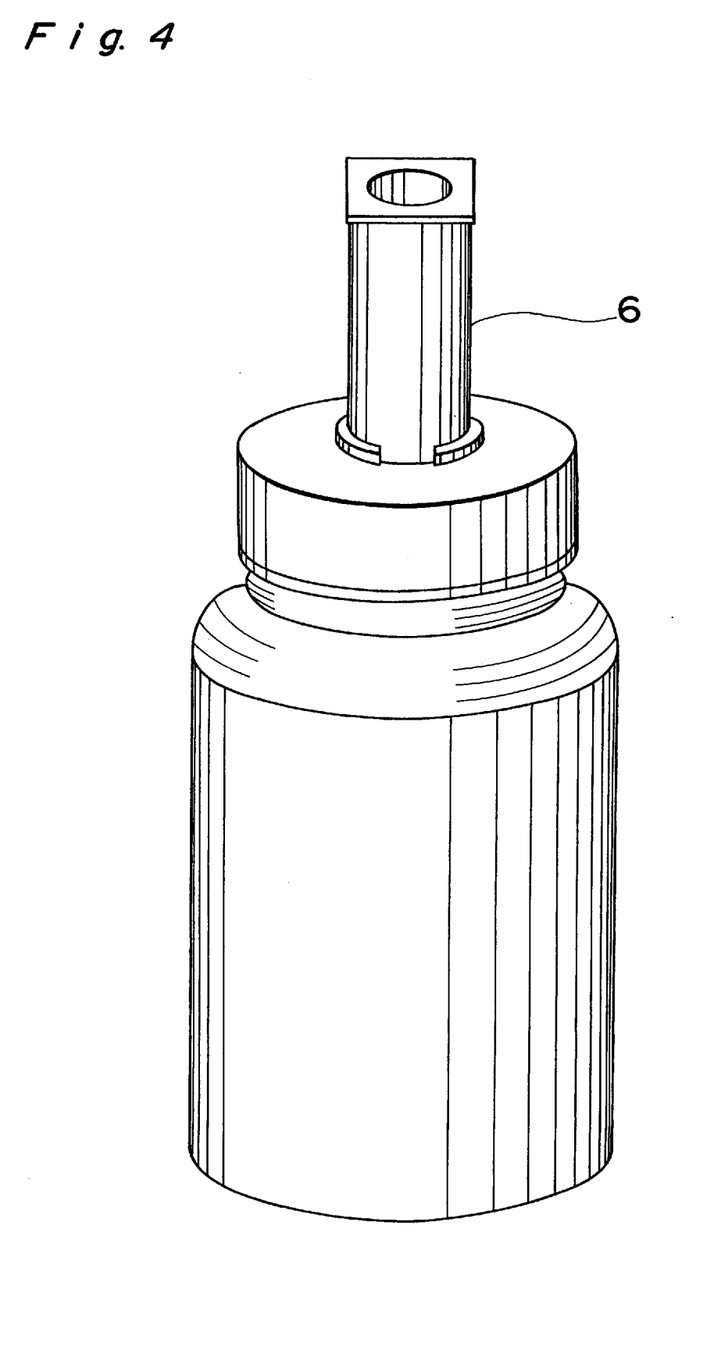
FIG. 4 is an perspective view of the waste container of FIG. 1 with a blood collection needle holder inserted therein.
Figure 5:
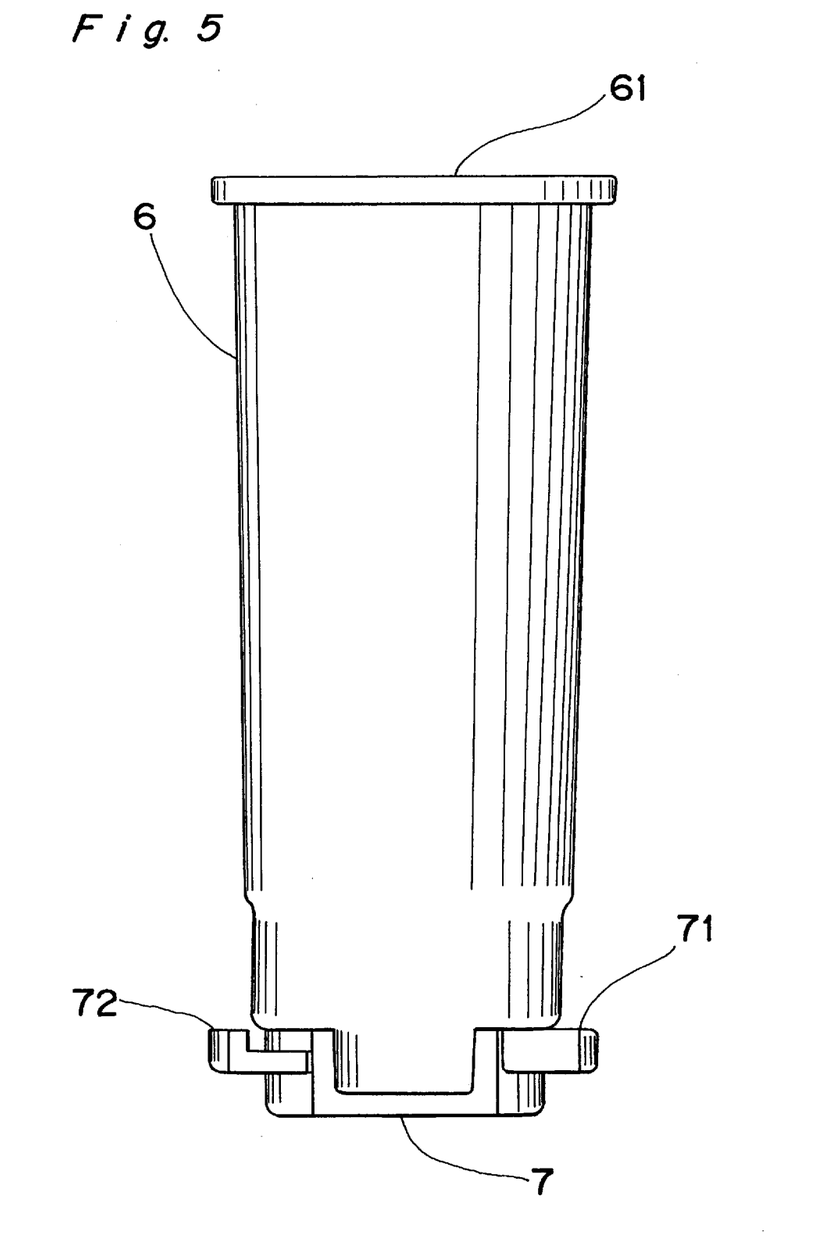
FIG. 5 is a side view of the holder shown in FIG. 4.

FIG. 4 illustrates the holder 6 being inserted in the waste container shown in FIG. 1, while FIG. 5 illustrate a side view of the holder 6 shown in FIG. 4.

Figure 6:
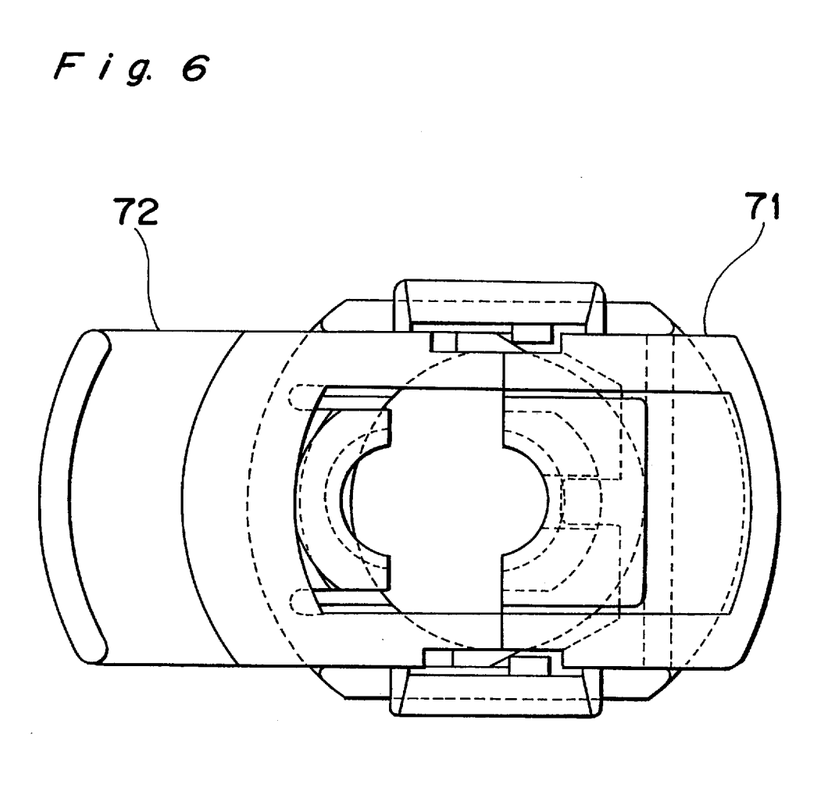
FIG. 6 is a bottom view of the needle fixing means of the holder shown in FIG. 5, illustrating a disengageable state of the needle fixing means of the holder.
Figure 7:
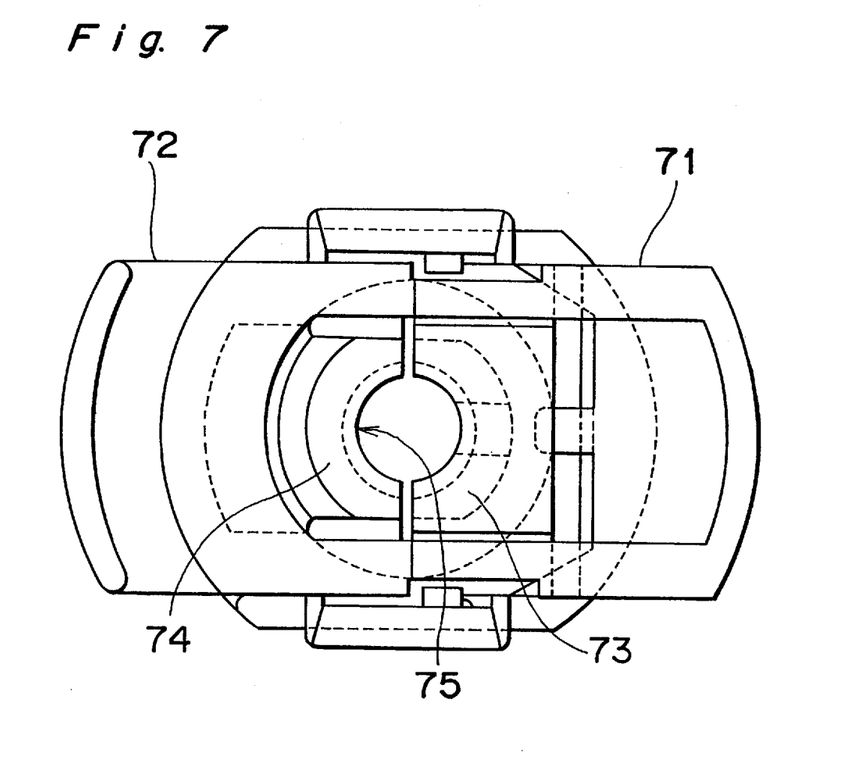
FIG. 7 is a bottom view of the needle fixing means similar to FIG. 5, illustrating an engageable state of the needle fixing means of the holder.

The holder 6 is formed into a cylindrical member opened at one end but closed at the other end. The holder 6 is provided at its closed end with a blood collection needle fixing means 7 including two sliding members 71,72 slidable along the closed end wall of the holder 6. The two sliding members 71 and 72 are so constructed as to be slidable between engageable and disengageable positions respectively illustrated in FIGS. 6 and 7. When one of the sliding members (hereinafter referred to as the "first sliding members 71") is moved toward the other sliding member (hereinafter referred to as the "second sliding member 72"), these sliding members are slid along the closed end wall of the holder 6 and reached to the disengageable position of FIG. 6 where they are disengageable with a hub (not illustrated) of the needle. On the other hand, when the second sliding member 72 is moved toward the fist sliding member 71, they are slid and reached to the engagable position of FIG. 7 where they are engagable with the hub of the needle. The needle fixing means 7 further includes a pair of half ring members 73 and 74. One half ring member 73 is fixed to the top wall of the holder 6, while the other half ring member 74 is fixed to the second sliding member 72 so that they form a threaded bore 75 for engagement with the needle when the sliding members 71 and 72 are reached to the engageable position as shown in FIG. 7.

When sampling the blood from a patient, a blood collection needle is attached to the holder 6 and pierced into an intravenous vein of the patient, and then a vacuum blood sampling tube (not illustrated) is inserted into the holder 6 through an open end 61 of the holder 6.

After completing the blood sampling, the needle is removed from the holder 6 by the waste container of the present invention. This operation will be explained below, making reference to FIGS. 2 to 7. The holder 6 with the needle is inserted into the waste container through the holder insertion portion 31 so that the position of the first sliding member 71 coincides with the first notched portion 33 of the needle-removing means 3. Since the sliding members 71 and 72 are held in the engageable position of FIG. 7 where the hub of the needle is engaged with the threaded bore 75 of the holder 6, the first sliding member 71 is brought into contact with the slanted portion 35 by pushing the holder 6 downward, and then forced to slide toward the second sliding member 72 by the slanted portion 35. For this reason, the holder 6 is moved to the disengageable position as shown in FIG. 6, and allows the needle to fall into the container body 1. Since the second sliding member 72 is slid together with the first sliding member 71, the downward movement of the holder 6 is stopped when the second sliding member 72 is collided with the bottom of the second notched portion 34 in the holder suspension section 32.

The slanted portion 35 extending from the first notched section 33 may be provided within the holder insertion portion 31. Further, the second notched portion 34 is formed at a level deeper than the slanted portion 35 in order to bring the holder 6 into a condition disengageable with the hub of the needle by allowing the first sliding member 71 of the needle fixing means 7 to slide toward the second sliding member 72. However, there is no limit on the depth of the second notched portion 34, provided that the first sliding member 71 is allowed to slide to a position where the holder 6 is disengageable with the needle.

The bottom of the second notched portion 34 must be located within the holder suspension section 32 with an inner diameter smaller than the outer diameter of the holder 6 to stop downward movement of the holder 6.

Further, the slanted portion 35 may be colored to indicate the insertion direction of the holder 6 definitely since it is required to allow the first sliding member 71 to coincide with the first notched portion 33 of the needle removing means 3 when inserting the holder 6 into the waste container.

Although there is no special limitation on an angle of inclination of the slanted portion 35, it is necessary the slanted portion 35 to have a certain inclination and a length to bring the holder 6 into a condition disengageable with the hub of the needle. Thus, the angle of inclination and length of the slanted portion are determined, taking account of the sliding distance of the first sliding member 71.

The container body 1 of the waste container is preferably provided with covering means over the opening 21 of the container body 1. The covering means prevents the needles which have been removed from the holder 6 and contained in the container body 1 from scattering when the waste container is overthrown accidentally.

Figure 8:
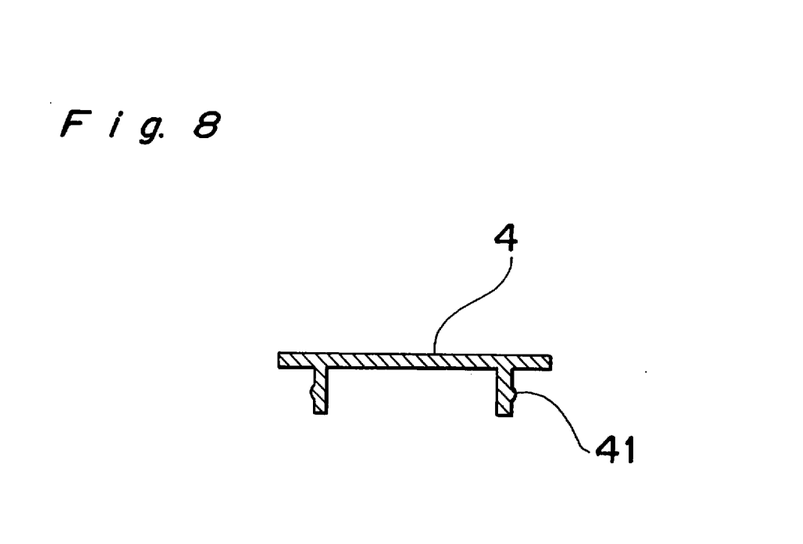
FIG. 8 is a cross section view illustrating an example of a covering means shown in FIG. 1.

As the covering means, a freely removable cap illustrated in FIG. 8 is generally used. The cap is preferably provided with at least one rib 41 on an outside wall of a skirt portion thereof. Also, a lid member 5 as illustrated in FIG. 9 may be used as the covering means for closing and opening the opening 21 of the lid body 2.

Figure 9:
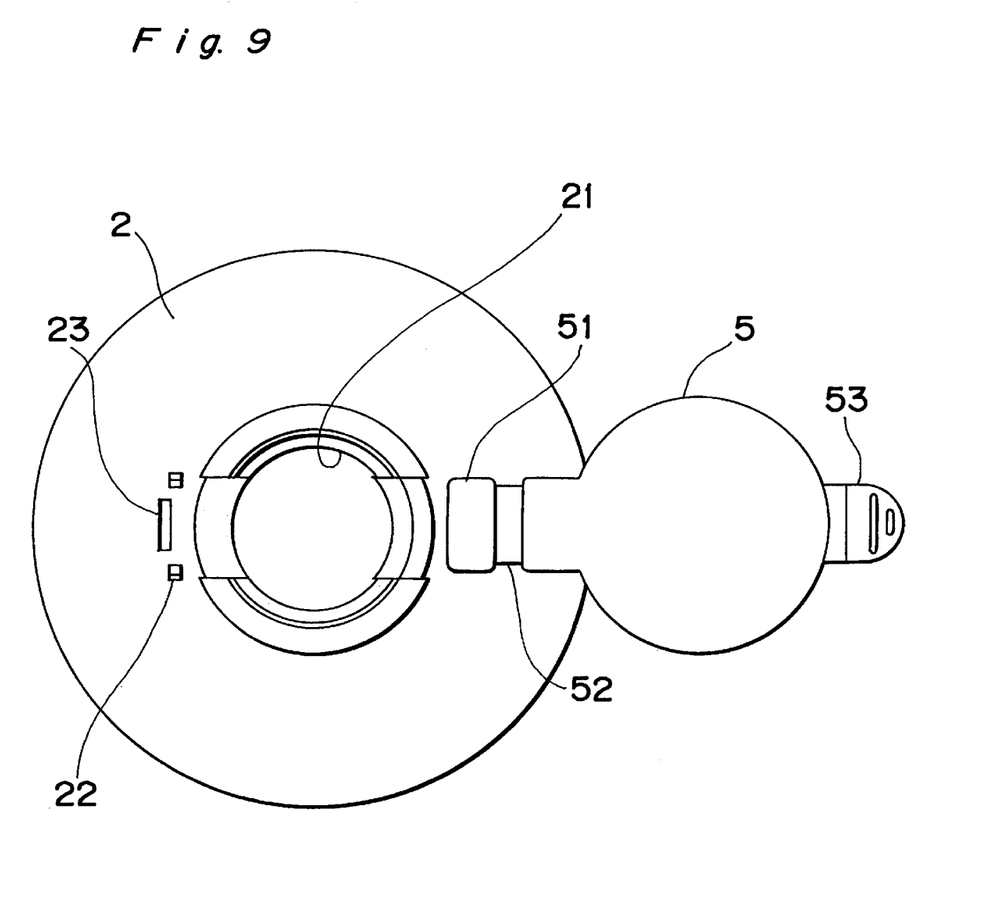
FIG. 9 is a plane view illustrating another embodiment of the covering means.
Figure 10:
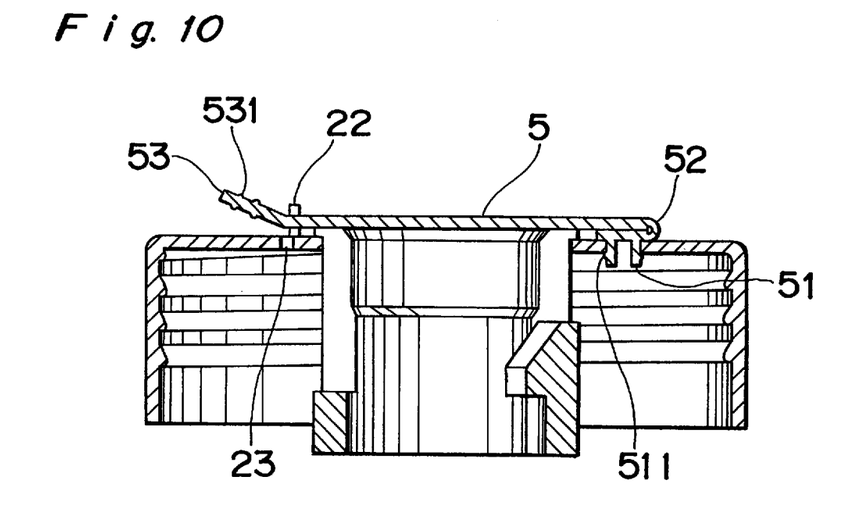
Fig. 10 is a schematic cross sectional view illustrating covering means of FIG. 9 being arranged on the lid body of FIG. 1.
Figure 11:
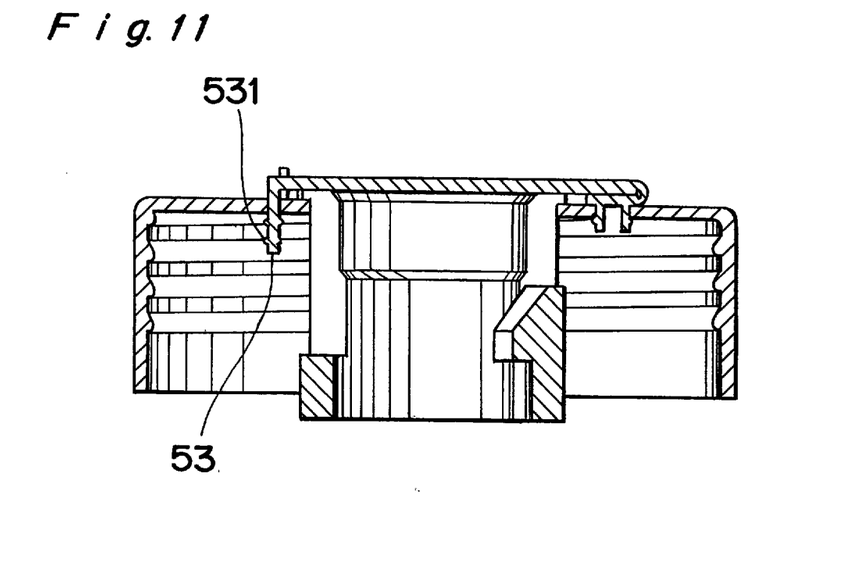
FIG. 11 is a view similar to FIG. 10, illustrating the covering means of FIG. 9 being fixed firmly to the lid body of FIG. 1.

As illustrated in detail in FIGS. 9–11, the lid member 5 has a fixing portion 51 for engagement with the lid body 2. This fixing portion 51 is connected to the lid member with a connecting portion 52. The fixing member 51 has a pair of leg portions each having a rib 511 provided on an outer wall thereof, as shown in FIG. 10.

The lid member 5 may be provided with a tab or grip portion 53 to assist operation thereof. Further, the lid body 2 may be provided with a pair of anchoring projections 22 extending upwardly from the top wall thereof and facing to one another, spaced by a distance equal to a width of the tab or grip portion 53, so that the grip portion 53 is held between them by friction fitting when folding back the lid member 5 to close the opening 21 of the lid body 2. Even if the operation removing the needle from the holder 6 is done repeatedly, the lid member 5 can be held between the anchoring means 22 of the lid body 2 whenever the removal operation of the needle is finished. Thus, the waste container keeps safe even if the waste container is fallen down accidentally.

As shown in FIG. 10 and FIG. 11, the grip portion 53 may be provided with projections 531 on one side or both sides of a distal portion thereof and the lid body 2 may be provided with a slit or slender oblong opening 23 for insertion of the grip portion 53. The provision of projections 531 on both sides of the grip portion makes it possible to keep the lid member 5 from being never released from the lid body 2 once the grip portion 53 has been inserted into the oblong opening 23.

As will be understood from the above, the waste container of the present invention makes it possible to remove the needle from the holder with ease and surely as well as to receive the removed needle therein. Further, the waste container of the present invention is provided with a covering means at a top of the opening of the waste container, thus making it possible to avoid scattering of the used needles in the waste container even if the waste container is accidentally fallen down. In addition, it is possible to carry the waste container to a certain disposition safely since the opening of the waste container can be sealed. Accordingly, infection due to accidental stick of the used needle can be prevented surely.

Although the present invention has been fully described in connection with the preferred embodiments thereof with reference to the accompanying drawings, it is to be noted that various changes and modifications are apparent to those skilled in the art. Such changes and modifications are to be understood as included within the scope of the present invention as defined by the appended claims unless they depart therefrom.

I claim:

1. An infectious waste container for blood collection needles, comprising:
   a container body with a mouth at a top thereof;
   a lid body attached to the mouth of said container body and provided in a top wall thereof with an opening; and
   needle-removing means arranged in the opening of said lid body for removing a blood collection needle from needle fixing means of a blood collection needle holder;

said needle-removing means comprising a cylindrical member including a holder insertion section and a holder suspension section, said holder insertion section being so formed as to have an inner diameter larger than an outer diameter of said holder, while said holder suspension section being so formed as to have an inner diameter smaller than the outer diameter of said holder, said cylindrical member being axisymmetrially provided with first and second notched portions extending from the holder insertion section to the holder suspension section, said first notched portion being stretched to a downwardly slanted portion protruded inwardly from a bottom of said first notched portion, said first notched portion being terminated at a level where the needle fixing means of said holder does not come into contact with the inner wall of the cylindrical member when said holder is inserted thereinto, while the second notched portion being so formed as to be deeper than the level of the slanted portion by a certain distance and terminated within the holder suspension section.

2. The infectious waste container according to claim 1, wherein said opening of the lid body is provided with a covering means.

3. The infectious waste container according to claim 1, wherein said covering means is a freely removable cap provided with at least one rib at a outer wall of its skirt portion.

4. The infectious waste container according to claim 1, wherein said covering means is a lid member adapted to open and close the opening of the lid body, said lid member having a fixing portion for engagement with the lid body and being connected to the fixing portion with a connecting portion.

5. The infectious waste container according to claim 1, wherein said lid member is provided with a grip portion and wherein the top wall of the lid body is provided with engaging means projecting therefrom so that the lid member is lightly engaged with the lid body.

6. The infectious waste container according to claim 1, wherein said grip portion is provided with a projection, and wherein the top wall of the lid body is provided with a hole in which said projection is fitted so that the covering means closes the lid body firmly.

* * * * *